US011077087B2

(12) United States Patent
Auclair (10) Patent No.: US 11,077,087 B2
(45) Date of Patent: Aug. 3, 2021

(54) COMPOSITIONS COMPRISING DIHYDROQUERCETIN FOR USE IN METHODS FOR TREATING HERPES

(71) Applicant: BIONOOX SUISSE SA, Cadempino (CH)

(72) Inventor: Christian Auclair, Saint-Arnoult en Yvelines (FR)

(73) Assignee: BIONOOX SUISSE SA, Cadempino (CH)

( * ) Notice: Subject to any disclaimer, the term of this patent is extended or adjusted under 35 U.S.C. 154(b) by 454 days.

(21) Appl. No.: 15/558,587

(22) PCT Filed: Mar. 18, 2016

(86) PCT No.: PCT/EP2016/056054
§ 371 (c)(1),
(2) Date: Sep. 15, 2017

(87) PCT Pub. No.: WO2016/146843
PCT Pub. Date: Sep. 22, 2016

(65) Prior Publication Data
US 2018/0055815 A1   Mar. 1, 2018

(30) Foreign Application Priority Data

Mar. 18, 2015   (EP) .................................. 15159744

(51) Int. Cl.
| | | |
|---|---|---|
| *A61P 31/22* | (2006.01) | |
| *A61K 9/00* | (2006.01) | |
| *A61K 31/353* | (2006.01) | |
| *A61K 31/355* | (2006.01) | |
| *A61K 31/045* | (2006.01) | |
| *A61K 31/352* | (2006.01) | |
| *A61K 9/06* | (2006.01) | |
| *A61K 45/06* | (2006.01) | |

(52) U.S. Cl.
CPC .......... *A61K 31/352* (2013.01); *A61K 9/0014* (2013.01); *A61K 9/0053* (2013.01); *A61K 9/06* (2013.01); *A61K 31/045* (2013.01); *A61K 31/353* (2013.01); *A61K 31/355* (2013.01); *A61K 45/06* (2013.01); *A61P 31/22* (2018.01)

(58) Field of Classification Search
CPC ..... A61P 31/22; A61K 31/355; A61K 31/353; A61K 31/045; A61K 9/0014
See application file for complete search history.

(56) References Cited

U.S. PATENT DOCUMENTS

| | | |
|---|---|---|
| 9,271,956 B2 | 3/2016 | Auclair |
| 9,956,200 B2 | 5/2018 | Auclair et al. |
| 2002/0150600 A1 | 10/2002 | Buchholz et al. |
| 2005/0249761 A1 | 11/2005 | Buenger et al. |
| 2011/0159106 A1* | 6/2011 | Desjonqueres ...... A61K 9/0014 424/604 |

FOREIGN PATENT DOCUMENTS

| | | | |
|---|---|---|---|
| EP | 1 205 177 A2 | 5/2002 | |
| EP | 2 700 413 A1 | 2/2014 | |
| EP | 2700413 A1 * | 2/2014 | ............. A61K 47/06 |
| FR | 263556 A3 | 2/2012 | |
| JP | 07-223933 A | 8/1995 | |
| JP | 2000-026263 A | 1/2000 | |
| RU | 2 382 635 C1 | 2/2010 | |
| WO | 93/25209 A1 | 12/1993 | |
| WO | 00/02554 A1 | 1/2000 | |
| WO | 03/051287 A2 | 6/2003 | |
| WO | 03/084553 A1 | 10/2003 | |
| WO | 2014/029780 A1 | 2/2014 | |

OTHER PUBLICATIONS

Aquino, R., et al., "4. Structure and Biological Activity of Triterpenoids and Aromatic Compounds from Medicinal Plants; 4.6 Antiviral Activity," Structure and Chemistry (Part D), vol. 17, Jan. 1995, p. 145.
Kirchner, et al., "Flavonoids and 5-Aminosalicylic Acid Inhibit the Formation of Neutrophil Extracellular Traps," Mediators of Inflammation, vol. 138, No. 7, Jan. 2013, pp. 2177-14.
Bito, et al., "Flavonoids Differentially Regulate IFNgamma-induced ICAM-1 Expression in Human Keratinocytes: Molecular Mechanisms of Action," FEBS Letters, vol. 520, No. 1-3, Jun. 2002, pp. 145-152.
Zhu, et al., "Anti-Inflammatory Constituents from Inula Japonica," Zhongguo Zhongyao Zazhi, vol. 39, No. 1, Jan. 2014, p. 88.
Wang, et al., "Prevention of Macrophage Adhesion Molecule-1 (Mac-1)-Dependent Neutrophil Firm Adhesion by Taxifolin Through Impairment of Protein Kinase-Dependent NADPH Oxidase Activation and Antagonism of G Protein-Mediated Calcium Influx," Biochemical Pharmacology, vol. 67, No. 12, Jun. 2004, pp. 2251-2262.
Breinholt, et al., "Structure-Cytotoxicity Relationships for Dietary Flavonoids," In Vitro and Molecular Toxicology, vol. 11, No. 2, Jul. 1998, pp. 193-206.
Micali, et al., "Use of an Anti-Inflammatory Cream in Childhood Psoriasis (Poster)," 5th European Congress on Psoriasis & 7th International Psoriasis Symposium, Sep. 1998, (abstract book), p. 159.
Kadir, et al., "α-Bisabolol, a Possible Safe Penetration Enhance for Dermal and Transdermal Therapeutics," International Journal of Pharmaceutics, vol. 70, No. 1-2, Mar. 1991, pp. 87-94.
Mizutani, et al., "Seitai no Sanka to Kosankaseibun no Kaihatsu to Oyo," Fragrance Journal, 1997, 4:81-87.
Lyu, et al., "Antiherpetic Activities of Flavonoids Against Herpes Simplex Virus Type 1 (HSV-1) and Type 2 (HSV-2) In Vitro," Arch. Pharm. Res., vol. 28, No. 11, 2005, pp. 1293-1301.
International Search Report issued in Application No. PCT/EP2013/067333, dated Oct. 21, 2013.

(Continued)

*Primary Examiner* — Theodore R. Howell
(74) *Attorney, Agent, or Firm* — Nixon & Vanderhye (57) ABSTRACT

Disclosed is the use of a composition including dihydroquercetin and optionally α-tocopherol and/or bisabolol for treating herpes infection. Also disclosed is the use of such a composition for treating inflammation induced by herpes infection in mucosa, as well as a method for treating HSV infection and the associated inflammation.

8 Claims, 3 Drawing Sheets

(56) References Cited

OTHER PUBLICATIONS

International Search Report issued in Application No. PCT/EP2016/056054, dated May 12, 2016.
International Search Report issued in Application No. PCT/EP2015/053444, dated Mar. 30, 2015.

* cited by examiner

COMPOSITIONS COMPRISING DIHYDROQUERCETIN FOR USE IN METHODS FOR TREATING HERPES

FIELD OF INVENTION

The present invention relates to the treatment of herpes infection and/or of mucosal inflammation induced by herpes infection, especially herpes simplex virus type 2 (HSV-2) infection. In particular, the present invention relates to a composition comprising dihydroquercetin and optionally α-tocopherol and/or bisabolol for use for topical treatment of symptoms linked to herpes infection, especially HSV-2 infection or mucosal inflammation triggered by herpes infection, especially HSV-2 infection. Also, this invention relates to a method for treating a subject in need thereof, infected by herpes virus, comprising topically applying a composition comprising dihydroquercetin and optionally α-tocopherol and/or bisabolol on infected mucosal areas.

BACKGROUND OF INVENTION

Herpes is due to two types of herpes simplex viruses (HSV), type 1 and type 2. Both types are highly contagious and can be passed easily from one person to another by direct contact. At least 8 out 10 people who carry the virus are unaware that they have been infected because there are often few or no initial symptoms. However, certain triggers can activate the virus, causing an outbreak of herpes. The main triggering situations are: stress, illness, fever, sun exposure, menstrual periods and surgery.

Herpes simplex viruses are ubiquitous, host-adapted pathogens that cause a wide variety of disease states. Up to 80% of herpes simplex infections are asymptomatic. Symptomatic infections can be characterized by significant morbidity and recurrence. In immunocompromised hosts, infections can cause life-threatening complications.

The prevalence of HSV infection worldwide has increased over the last several decades, making it a major public health concern. Prompt recognition of HSV infection and early initiation of therapy are of utmost importance in the management of the disease.

Genital Herpes

Genital herpes is a common infection caused by herpes simplex virus of type 2. It causes painful blisters on the genitals and the surrounding areas. Genital herpes can be passed to others through intimate sexual contact and can affect any mucous membrane (moist lining). Genital herpes is a chronic disease, the virus remaining in the body and can become active again following various circumstances. The average rate of recurrence is four to five times in the first two years after being infected. However, over time, it becomes active less frequently and each outbreak becomes usually less severe. Genital herpes can cause problems during pregnancy. These complications can be more serious depending on whether you already have genital herpes, or develop it for the first time while pregnant.

The Centers for Disease Control and Prevention (CDC) estimate that, annually, 776 000 people in the United States get new herpes infections. Nationwide, 16% of persons aged 14 to 49 years have HSV-2 infection.

HSV-2 infection is more common among women than among men (20.9% versus 11.5% in 14 to 49 year olds). Infection is more easily transmitted from men to women than from women to men. In the United States, an estimated 8.1% of 14-49 year olds infected with HSV-2 have never received a clinical diagnosis.

There is no cure for herpes. Antiviral medications can, however, prevent or shorten outbreaks during the period of time the person takes the medication. In addition, daily suppressive therapy (i.e. daily use of antiviral medication) for herpes can reduce the likelihood of transmission to partners.

Several clinical trials have tested vaccines against genital herpes infection, but there is currently no commercially available vaccine. One vaccine trial showed efficacy among women whose partners were HSV-2 infected, but only among women who were not infected with HSV-1. A subsequent trial testing the same vaccine showed some protection from genital HSV-1 infection, but no protection from HSV-2 infection (Belshe et al, N Engl J Med. 2012, 366(1):34-43).

Accordingly, there is still a need for antiviral treatment of herpes, and more especially for genital herpes. Flavonoids are known to have an antiviral activity (Wang et al, Adv Exp Med Biol. 1998, 439:191-225). Because of the worldwide spread of HIV, since 1980s, the investigations of the antiviral activity of flavonoids have mainly focused on HIV. The discovery and the development of flavonoids as anti-HIV agents have expanded in the past two decades. Some of the viruses reported to be affected by flavonoids are herpes simplex virus (Wang et al, Adv Exp Med Biol. 1998, 439:191-225; Lyu et al, Arch Pharm Res. 2005, 28(11): 1293-301), respiratory syncytial virus and adenovirus. However, by far most of the studies were performed in vitro and little is known about the antiviral effect of flavonoids in vivo, even for the treatment of HIV. Moreover, to the Applicant knowledge, there is no clinically validated flavonoid drug for antiviral treatments, and in particular for treating herpes infection.

The Applicant surprisingly found that dihydroquercetin (DHQ), a natural compound of the flavonoid family, inhibit neutrophils and mast cells which are known to play a key role in the development of inflammation associated to HSV infection.

Therefore, the invention relates to compositions comprising DHQ for use in a method for treating HSV infection-related symptoms, especially genital herpes symptoms, and the associated inflammation of the mucosa.

SUMMARY

The present invention relates to a composition comprising dihydroquercetin, and optionally α-tocopherol and/or bisabolol for use for topically treating herpes, especially HSV-2, infection, more specifically for topically treating symptoms linked to HSV-2 infections, even more specifically for topically treating mucosal HSV-2 symptoms, i.e. mucosal areas infected by HSV-2 infection. In one embodiment, the composition is for treating mucosal inflammation induced by HSV-2 infection.

In one embodiment, the mucosa is genital, or in other words, herpes is genital herpes.

According to one embodiment, the composition for use in the invention is such that the concentration of dihydroquercetin in the composition ranges from 0.1% to 10% in weight of the total weight of the composition (w/w), preferably from 0.5% to 8% w/w, preferably from 1% to 5% w/w.

In an embodiment of the invention, the said composition further comprises α-tocopherol.

In a specific embodiment, the composition for use in the invention is such that concentration of said α-tocopherol ranges from 0.05% to 5% in weight of the total weight of the composition (w/w), preferably from 0.1% to 3% w/w, preferably from 0.5% to 2% w/w.

In an embodiment, the composition for use in the invention further comprises bisabolol.

In a particular embodiment, the composition for use in the invention is such that the concentration of bisabolol ranges from 0.02% to 5% in weight of the total weight of the composition (w/w), preferably from 0.1% to 2% w/w, preferably from 0.2% to 1% w/w.

In an embodiment, the composition for use in the invention further comprises an acceptable vehicle, preferably a mucosal compatible base; preferably wherein said composition comprises at least one compound selected from the group comprising animal fat, vegetable fat, higher alcohols, glycols or mixtures thereof.

In an embodiment, the composition for use in the invention further comprises at least one component selected from the group comprising surfactants, pigments, stabilizers, emollients, humectants or mixtures thereof.

In one embodiment, the composition for use according to the invention comprises from 0.1% to 10% w/w DHQ, from 0.05% to 5% w/w α-tocopherol, from 0.02% to 5% w/w bisabolol and a mucosal-compatible base.

In one embodiment, the composition for use according to the invention comprises about 5% w/w DHQ, about 1% w/w α-tocopherol, about 0.2% w/w bisabolol and a mucosal-compatible base.

In an embodiment, the composition for use in the invention is a cream, a gel, an ointment, a solution, an emulsion, especially an oil-in-water emulsion, a mask, a stick, a milk, a lotion, a serum, a paste, a foam or a suspension, and preferably a cream or a stick.

In an embodiment, the composition for use in the invention is administered in combination with another treatment for herpes, preferably an oral treatment for herpes, especially HSV-2.

In a particular embodiment, the composition in the invention comprises dihydroquercetin and optionally α-tocopherol and/or bisabolol for use as a companion cosmetic composition in the treatment of herpes infection.

Definitions

In the present invention, the following terms have the following meaning:

"subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a herpes infection. In one embodiment, the subject is an adult (for example a subject above the age of 18). In another embodiment, the subject is a child (for example a subject below the age of 18). In one embodiment, the subject is a male. In another embodiment, the subject is a female.

"treating" or "treatment" refers to both therapeutic treatment and prophylactic or preventative measures; wherein the object is to prevent or slow down (lessen) or alleviate herpes infection related symptoms. Those in need of treatment include those already with herpes infection as well as those prone to have herpes infection or those in whom herpes infection is to be prevented. A subject or mammal is successfully "treated" for herpes infection if, after receiving a therapeutic amount of a composition for use according to the present invention, the patient shows observable and/or measurable reduction in or absence of one or more of the following: reduction in the number of pathogenic cells; reduction in the percent of total cells that are pathogenic; and/or relief to some extent, of one or more of the symptoms associated with herpes infection (including, without limitation, cold sores on or around the lips, in the mouth, on the nose, on the eyes, or blisters or itching on the genitals and the surrounding areas); reduced morbidity and mortality, and improvement in quality of life issues. The above parameters are readily measurable by routine procedures familiar to a physician.

"therapeutically effective amount" means the level or amount of the composition of the invention that is aimed at, without causing significant negative or adverse side effects to the target, (1) delaying or preventing the onset of herpes infection; (2) slowing down or stopping the progression, aggravation, or deterioration of one or more symptoms of herpes infection; (3) bringing about ameliorations of the symptoms of herpes infection or alleviating the symptoms of herpes infection; or (4) reducing the severity or incidence of herpes infection's symptoms. A therapeutically effective amount may be administered prior to the onset of herpes infection, for a prophylactic or preventive action. Alternatively or additionally, the therapeutically effective amount may be administered after initiation of herpes infection's symptoms, for a therapeutic action or maintenance of a therapeutic action.

"therapeutic composition" describes a composition, having the capacity, when administered in a suitable amount, of slowing down or stopping the progression, aggravation, or deterioration of one or more symptoms of herpes or of alleviating the symptoms of herpes.

"pharmaceutically acceptable carrier or excipient" refers to an excipient or carrier that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, injected preparations should meet sterility, pyrogenicity, general safety and purity standards as required by regulatory offices, such as, for example, FDA Office or EMA.

"about" preceding a figure means plus or less 10% of the value of said figure.

"cosmetic composition" refers to a composition intended to be in contact with the diverse superficial parts of the human body, in particular the mucosa including the lips, the external genital parts, or any mucous membranes, in sight, exclusively or mainly, to clean them, to perfume them, to protect them, to maintain them in good condition, to modify their aspect or to correct the body odors. In one embodiment, a cosmetic composition of the invention aims at reducing or preventing the appearance of the visible mucosal signs of herpes infection, thereby maintaining the mucosa in good condition and/or or modify their aspects.

"cosmetically acceptable" refers to a component that is suitable for use in contact with the mucosa including the lips, the external genital parts, or any mucous membranes without undue adverse side effects (such as toxicity, irritation, allergic response, and the like).

"cosmetically acceptable base" refers to a cosmetically acceptable vehicle comprising a lipophilic component.

"vehicle" refers to a substance with which the component of interest is mixed or wherein the component of interest is dissolved. In an embodiment, the vehicle may be a cosmetically acceptable base.

DETAILED DESCRIPTION

In a first aspect, this invention relates to a composition comprising dihydroquercetin (DHQ) and optionally α-tocopherol and optionally bisabolol for use for treating, including alleviating, HSV infection's symptoms.

In a second aspect, this invention relates to a composition comprising dihydroquercetin (DHQ) and optionally α-tocopherol and optionally bisabolol for use for treating the inflammation in the mucosal infected areas, i.e. the term "treating herpes infection" or "treatment HSV infection's symptoms" comprises treating the inflammation in the mucosal infected areas due to, or associated with, herpes infection, especially HSV-2 infection. By "mucosa infected areas" is meant any part of the body where inflammation, cold sores and/or blisters caused by herpes are present and may break out. Examples of such infected areas are, without limitation, the mucosa of lips, mouth, nose, eyes, genitals and surrounding areas. DHQ is the common name of 3,3', 4',5,7-pentahydroxyflavone dehydrate, also called 2-(3,4-dihydroxyphenyl)-3,5,7-trihydroxy-4H-1-benzopyran-4-one dehydrate, also known as taxifolin. DHQ is a valuable alternative to quercetin as it is characterized by a great chemical stability with conserved significant biological and pharmacological properties and by its safety. DHQ has been identified as a powerful antioxidant, as safe and as a natural preservative.

In one embodiment, DHQ is extracted from a type of larch wood, preferably from Siberian larch. In an embodiment, DHQ containing powder contains at least 96% w/w by weight of DHQ and corresponds to the technical requirements and sanitary rules on the basis of analytical and microbiological reports.

In one embodiment of the present invention, the concentration of DHQ in the composition for use in the invention ranges from 0.1% to 10% w/w (i.e. in weight, by weight of the total composition), preferably from 0.5% to 8% w/w, more preferably from 1% to 5% w/w.

In a particular embodiment, the composition for use of the invention comprises DHQ and α-tocopherol.

α-Tocopherol, commonly named vitamin E, has many biological functions, the antioxidant function being considered as the most important one. Furthermore, it is lipid-soluble. It performs its function as antioxidant on connection with the glutathione peroxidase pathway and it protects cell membrane from oxidation by reacting with lipid radicals produced during the lipid peroxidation chain reaction. This process would remove the reactive free radical intermediates and prevent the oxidation chain reaction from continuing. The resulting α-tocopheroxyl radicals may be converted back to the reduced form through reduction by other oxidants such as ascorbate, retinol or ubiquinol, as well as DHQ. Without willing to be bound by a theory, the Applicant suggests that α-tocopherol may favor the recycling of DHQ under its active phenolic form.

In one embodiment, the concentration in the composition of the invention of α-tocopherol is ranging from 0.05% to 5% w/w in weight by weight of the total composition, preferably ranging from 0.1% to 3% w/w, more preferably from 0.5% to 2% w/w, even more preferably about 1% w/w.

In another embodiment, the composition for use of the invention comprising DHQ and α-tocopherol further comprises bisabolol.

Bisabolol (6-methyl-2-(4-methyl-3-cyclohexen-1-yl)-5-hepten-2-ol, or 1-methyl-4-(1,5-dimethyl-1-hydroxyhex-4(5)-nyl)cyclohexen-1) is a sesquiterperne that is found in various plants, including herbal tea and chamomile. The most important known effects of bisabolol are anti-inflammatory, wound healing, anti-bacterial, anti-mycotic and anti-phlogistic properties. Therefore, it is widely used in cosmetic and personal care products. Especially, bisabolol may be used to enhance the transepidermal penetration, in other words it may be used to increase diffusivities across the modified skin barrier (Kadir et al., Int. J. Phann., 1991, 70:87-94). In the present invention, bisabolol is used as a vehicle of DHQ and/or α-tocopherol and is thought to facilitate the diffusion of DHQ and/or α-tocopherol to the dermal area.

In one embodiment, the concentration of bisabolol is ranging from 0.02% to 5% w/w in weight by weight of the total composition, preferably ranging from 0.1% to 2% w/w, more preferably from 0.2% to 1% w/w, even more preferably about 0.2% w/w.

In one embodiment, the composition for use of the invention comprises or consists of DHQ, α-tocopherol and bisabolol, in association with any acceptable vehicle. According to one embodiment, the composition for use in a method for treating HSV-2 infection related symptoms, especially HSV-2 related mucosal inflammation, according to the invention, comprises dihydroquercetin (DHQ), α-tocopherol and bisabolol, in association with an acceptable vehicle, especially a pharmaceutically acceptable vehicle.

In one embodiment, the composition for use in a method for treating HSV-2 infection related symptoms, especially HSV-2 related mucosal inflammation, according to the invention, comprises:
  from 0.1% to 10% in weight of the total weight of the composition of dihydroquercetin, preferably from 0.5% to 8% w/w, more preferably from 1% to 5% w/w,
  from 0.05% to 5% w/w of α-tocopherol, preferably from 0.1% to 2.5% w/w, more preferably from 0.5% to 2% w/w, and
  an acceptable vehicle.

In one embodiment, the composition for use in a method for treating HSV-2 infection related symptoms, especially HSV-2 related mucosal inflammation, according to the invention, comprises:
  from 0.1% to 10% in weight of the total weight of the composition of dihydroquercetin, preferably from 0.5% to 8% w/w, more preferably from 1% to 5% w/w,
  from 0.02% to 5% w/w of bisabolol, preferably from 0.1% to 2% w/w, more preferably from 0.2% to 1% w/w, and
  an acceptable vehicle.

In one embodiment, the composition for use in a method for treating HSV-2 infection related symptoms, especially HSV-2 related mucosal inflammation, according to the invention, comprises:
  from 0.1% to 10% in weight of the total weight of the composition of dihydroquercetin, preferably from 0.5% to 8% w/w, more preferably from 1% to 5% w/w,
  from 0.05% to 5% w/w of α-tocopherol, preferably from 0.1% to 2.5% w/w, more preferably from 0.5% to 2% w/w,
  from 0.02% to 5% w/w of bisabolol, preferably from 0.1% to 2% w/w, more preferably from 0.2% to 1% w/w, and
  an acceptable vehicle.

According to one embodiment, the acceptable vehicle comprises at least one compound selected from the group comprising animal fat, vegetable fat, higher alcohols, glycols, mineral oil or a mixture thereof.

A non-limitative example of animal fat is stearic acid. Examples of vegetable fat include, but are not limited to linoleic acid, jojoba oil (also called oil *Simmondsia chinensis*), sweet almond oil, avocado oil or a mixture thereof. Examples of higher alcohols include, but are not limited to cetearyl alcohol, stearyl alcohol, cetylic alcohol. Examples of glycols include, but are not limited to propylene glycol. Examples of mineral oil include, but are not limited to paraffin oil.

According to one embodiment, the composition for use in a method for treating HSV-2 infection related symptoms, especially HSV-2 related mucosal inflammation, according to the invention, further comprises at least one component selected from the group comprising surfactants, pigments, stabilizers, emollients, humectants or a mixture of thereof. In an embodiment, the composition for use in a method for treating HSV-2 infection related symptoms, especially HSV-2 related mucosal inflammation, according to the invention, comprises zinc oxide and/or zinc carbonate.

Examples of surfactants include, but are not limited to PEG-100 stearate, PEG-20 stearate or a mixture thereof. Examples of stabilizers include, but are not limited to carbomer. Examples of pigments include, but are not limited to zinc oxide. Examples of emollients include, but are not limited to caprylic/capric tryglyceride, dicapryl ether, glyceryl stearate, glyceryl monostearate or a mixture thereof. Examples of humectants include, but are not limited to glycerin, sorbitol or a mixture thereof.

According to one embodiment, the composition for use in a method for treating HSV-2 infection related symptoms, especially HSV-2 related mucosal inflammation, according to the invention, further comprises perfume, such as for example citronellol, geraniol, limonene, cinnamyl alcohol, butyl phenyl methylpropional, or a mixture thereof.

According to one embodiment, the composition for use in a method for treating HSV-2 infection related symptoms, especially HSV-2 related mucosal inflammation, according to the invention, further comprises preservatives such as, for example, imidazolidinyl urea.

According to one embodiment, the composition for use in a method for treating HSV-2 infection related symptoms, especially HSV-2 related mucosal inflammation, according to the invention, further comprises water.

In one embodiment, the composition for use in a method for treating HSV-2 infection related symptoms, especially HSV-2 related mucosal inflammation, according to the invention is designed for topical administration.

According to one embodiment, the composition for use in a method for treating HSV-2 infection related symptoms, especially HSV-2 related mucosal inflammation, according to the invention is under a form adapted to topical administration, such as, for example, in the form of a cream, a gel, an ointment, a solution, an emulsion, a mask, a milk, a lotion, a serum, a paste, a stick, a foam or a suspension. In a preferred embodiment, the composition of the invention is a cream or a stick. In another preferred embodiment, the composition for use in a method for treating HSV-2 infection related symptoms, especially HSV-2 related mucosal inflammation, according to the invention, is a gel. In a further preferred embodiment, the composition for use in a method for treating HSV-2 infection related symptoms, especially HSV-2 related mucosal inflammation, according to the invention, is an oil-in-water emulsion.

This invention also relates to a method for treating HSV-2 infection related symptoms in a subject in need thereof by topically administering an effective amount of a composition comprising dihydroquercetin (DHQ). In an embodiment, the composition further comprises α-tocopherol and/or bisabolol.

In one embodiment, HSV-2 infection related symptoms is an inflammation induced by herpes infection in mucosa.

In one embodiment, treating HSV-2 infection related symptoms means preventing and/or reducing visible signs of herpes infection. The term "visible signs of herpes infection" includes but is not limited to blisters in the mucosa of the lips, the nose, the eyes, or the genitals, and surrounding areas.

In one embodiment, treating HSV-2 infection related symptoms means preventing and/or limiting cutaneous or mucosal discomfort induced by herpes infection. Examples of discomfort induced by herpes infection include, but are not limited to, itching and pain.

In one embodiment, the subject is infected by herpes simplex virus of type 2.

In one embodiment, the subject is at risk of being infected by HSV-2. Examples of risks include, without limitation, contacts with persons infected with or HSV-2, in particular contacts with persons having active herpes infection.

In one embodiment, the herpes virus is inactive. In another embodiment, the herpes virus is active.

In one embodiment, the method of the invention comprises administering the composition to a subject experiencing an outbreak of herpes, especially HSV-2 infection, more especially HSV-2 related mucosal inflammation. In one embodiment, outbreak of herpes was caused by stress. In another embodiment, the outbreak of herpes was caused by illness. In another embodiment, the outbreak of herpes was caused by fever. In another embodiment, the outbreak of herpes was caused by sun exposure. In another embodiment, the outbreak of herpes was caused by menstrual periods. In another embodiment, the outbreak of herpes was caused by surgery. Therefore, in one embodiment, the subject is stressed, ill, have fever, exposed to sun, is in a menstrual period or underwent surgery.

In one embodiment, the outbreak of herpes is the first outbreak in the subject. In another embodiment, the outbreak of herpes is not the first outbreak in the subject, and is thus at least the second outbreak in the subject, such as, for example, the second, third, $4^{th}$, $5^{th}$, $6^{th}$, $7^{th}$, $8^{th}$ or more outbreak in the subject.

In one embodiment, the subject was not treated previously with another treatment for herpes infection. In another embodiment, the subject previously received one or more other treatments for herpes infection prior to be administered with the composition as described herein.

In one embodiment, the subject is resistant to at least one medication for treating herpes. Examples of such medications include, without limitation, docosanol, acyclovir, penciclovir, famciclovir, valaciclovir, and cidofovir. In one embodiment, the subject is resistant to at least one antiviral medication. Examples of antiviral medications include, without limitation, acyclovir, penciclovir, famciclovir, valaciclovir, and cidofovir. In a particular embodiment, the subject is resistant to acyclovir.

In one embodiment, the composition is administered while the subject is treated with acyclovir.

In one embodiment, the composition is a pharmaceutical composition. In an embodiment, the composition is a therapeutic composition. In one embodiment, the composition is a cosmetic composition. In one embodiment, the composition is a "companion cosmetic composition" or "add-on non-therapeutic composition".

In the meaning of this invention, "companion cosmetic composition" means cosmetic composition intended to assist patient in the management of their therapy-related cutaneous or mucosal discomfort. Advantageously, companion cosmetic compositions are safe, do not contain phototoxic and/or photosensibilizing components, show no toxicity. Moreover, companion cosmetic compositions do not affect effectiveness of the therapy.

In an embodiment, the composition according to the invention is for external use. In an embodiment, the use of the composition according to the invention requires the composition to be applied on inflamed mucosa.

In an embodiment, an amount of composition is applied which is sufficient to cover the afflicted area of the mucosa with a thin layer of the composition.

In an embodiment, the composition should be rubbed into the skin until little or no residue remains on the mucosa. In one embodiment, the composition is applied on the mucosa into a regular massage.

According to an embodiment, the composition may be applied one, two, three or more times a day, preferably three times a day. In one embodiment, the composition may be applied during 7, 14 or 21 days or until the visible symptoms of herpes infection disappear.

In an embodiment, the composition used in the method of the invention is stored in a container, preferably a glass container. In an embodiment, the glass container is sterilized using a dry heat sterilizer. In an embodiment, the container is a plastic container. In an embodiment, the plastic container is sterilized using UV irradiation using low-pressure "Hard Quartz Glass" UV Lamps.

In an embodiment, the composition for use of the invention is stable over one year in standard storage conditions.

The invention further relates to a method for treating HSV infection.

The invention also relates to a process for manufacturing the composition for use in the invention. In an embodiment, the process of the invention comprises a step of blending DHQ, α-tocopherol and/or bisabolol with an acceptable vehicle. In an embodiment, the process of the invention comprises a preliminary step of dissolving DHQ in jojoba oil (Oil *Simmondsia chinensis*), sweet almond oil or avocado oil before blending DHQ, α-tocopherol and/or bisabolol with an acceptable vehicle.

In an embodiment, the cosmetically acceptable vehicle is manufactured by any conventional method known in the art.

EXAMPLES

The present invention is further illustrated by the following examples.

Example 1: Compositions of the Invention

Topical compositions comprising 1, 2, 5 or 10% w/w DHQ, 0.5 or 1% w/w α-tocopherol and 0.1 or 0.2% w/w bisabolol, jojoba oil and a mucosal compatible vehicle.

| Composition number | DHQ (% w/w) | α-tocophérol (% w/w) | bisabolol (% w/w) | base |
|---|---|---|---|---|
| 1 | 1 | 0.5 | 0.1 | qsp 100% |
| 2 | 1 | 0.5 | 0.2 | qsp 100% |
| 3 | 1 | 1 | 0.1 | qsp 100% |
| 4 | 1 | 1 | 0.2 | qsp 100% |
| 5 | 2 | 0.5 | 0.1 | qsp 100% |
| 6 | 2 | 0.5 | 0.2 | qsp 100% |
| 7 | 2 | 1 | 0.1 | qsp 100% |
| 8 | 2 | 1 | 0.2 | qsp 100% |
| 9 | 5 | 0.5 | 0.1 | qsp 100% |
| 10 | 5 | 0.5 | 0.2 | qsp 100% |
| 11 | 5 | 1 | 0.1 | qsp 100% |
| 12 | 5 | 1 | 0.2 | qsp 100% |

Example 2: Effect of DHQ on the Activation of Polymorphonuclear Neutrophils

Materials and Methods

Neutrophils ($5 \times 10^5$) are suspended in 0.5 mL of Hanks balanced salt solution containing 10 μM luminol at 37° C. The cells are then stimulated with $10^{-6}$M fMLP (N-formylmethionyl-leucyl-phenylalanine). Chemiluminescence is recorded with a luminometer (Berthold-Biolumat LB937).

PMA (12-O-tetradecanoyl-phorbol-13-acetate, Consolidated Midland Corp., Brewster, N.Y.) is dissolved at 1 mg/ml in dimethyl sulfoxide. This stock solution maintains full biological activity for several months when stored at 25° C. in the dark. Unless otherwise specified, polymorphonuclear neutrophils (PMN), $10^6$/ml in BS-H, are put into plastic centrifuge tubes (Falcon No. 2070, Falcon Labware, Div. of Becton, Dickinson & Co., Oxnard, Calif.) and brought to 37° C. PMA stock solution is added to provide a final concentration of 100 ng/ml of PMA. "Resting" (control) cells are exposed to 1% (vol/vol) dimethyl sulfoxide. A chemiluminescence (using luminol) method is used to measure Reactive Oxygen species (ROS) production (Dang et al, J Clin Invest. 2006, 116(7):2033-43; Boussetta et al, Blood. 2010, 116(26):5795-802). Superoxide production is measured by the superoxide dismutase (SOD)-inhibitable ferricytochrome c reduction assay.

Results

Figure 1:
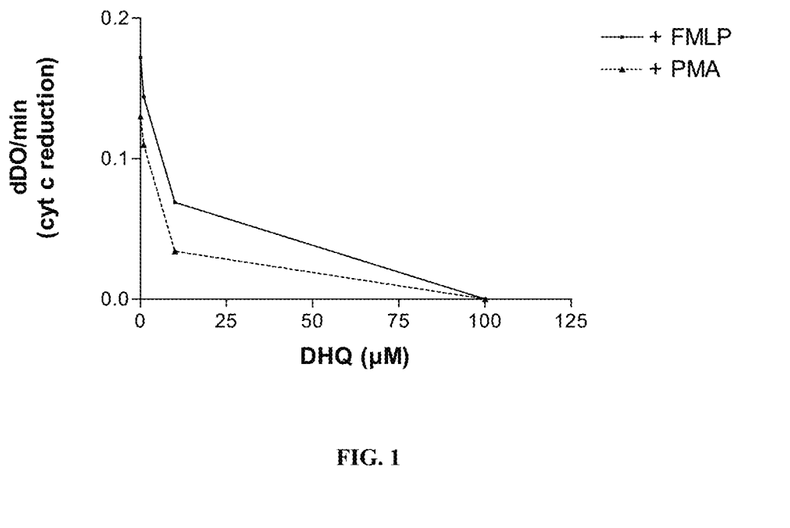
FIG. 1 is a graph showing the inhibitory effect of DHQ on the cytochrome c reduction (superoxide Anion production) resulting from the neutrophils activation by PMA or fMLP. Cytochrome c reduction is expressed in dDO/min. DHQ concentration is reported in μM. Numerical data are detailed in Table 1.

When activated by opsonized bacteria, zymozan, fMLP (Formyl-Methionyl-Leucyl-Phenylalanine) or PMA (phorbol myristate acetate), neutrophils undergo an oxidative burst resulting in the production of superoxide anion and subsequent hydrogen peroxide. The oxidative burst is mainly mediated by the NADPH oxidase activation, enzyme responsible of the superoxide anion production. The quantification of Superoxide anion by the measurement of the cytochrome c reduction (see Table 1 below and FIG. 1) shows that the addition of DHQ strongly inhibits cytochrome c reduction. This effect results either from the direct anion superoxide scavenging or from the inhibition of NADPH oxidase activation.

TABLE 1

Inhibitory effect of DHQ on the cytochrome c reduction (anion superoxide production) resulting from the neutrophils activation by PMA or fLMP.

| Neutrophils status: | Control | DHQ: 1 μM | DHQ: 10 μM | DHQ: 100 μM |
|---|---|---|---|---|
| Resting (dDO/min) | 0.004 | 0.000 | 0.036 | 0.086 |
| +fMLP (dDO/min) | 0.172 | 0.144 | 0.105 | 0.040 |
| +PMA (dDO/min) | 0.130 | 0.110 | 0.070 | 0.021 |

("dDO" stands for optic density variation)

In order to further investigate the effect of DHQ on the oxidative burst of neutrophils, ROS production was also measured by chemiluminescence for detecting both superoxide anion and hydrogen peroxide.

Neutrophils are triggered by PMA (100 ng/mL) in the presence of different concentrations of DHQ (0, 1, 10 and 100 μM) at 37° C. in Hanks buffer containing 10 μM luminol and chemiluminescence is measured by a chemiluminometer. Total chemiluminescence counts during 22.21 min. (integrals) corresponding to total ROS production are determined. The corresponding results are presented in Table 2 and FIG. 2.

TABLE 2

Figure 2:
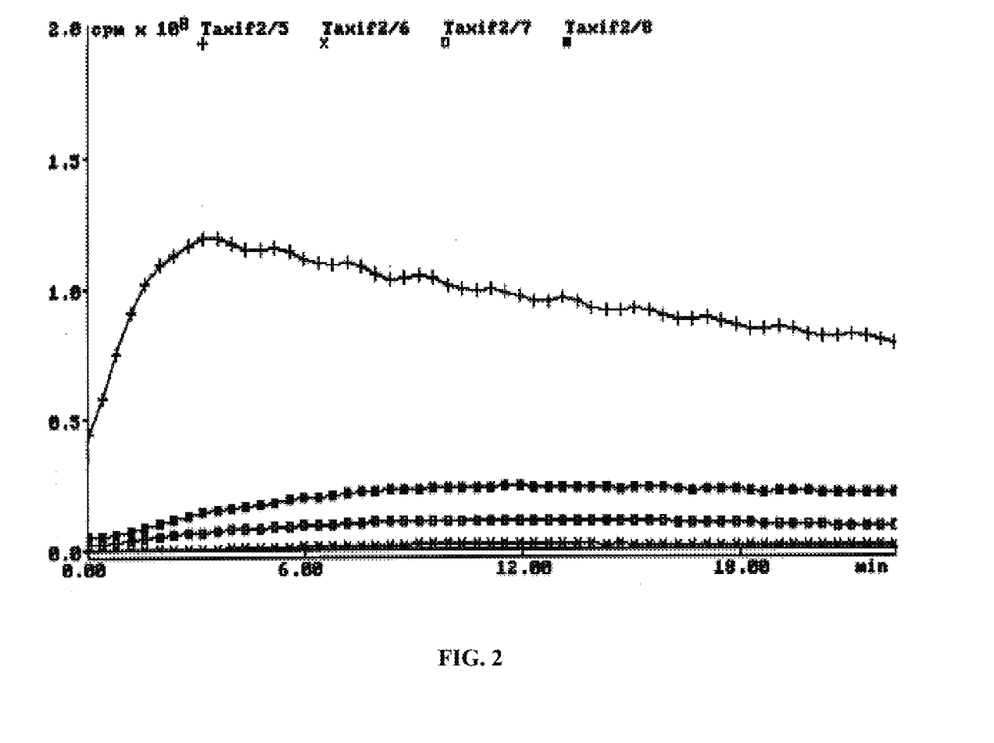
FIG. 2 is a graph showing the inhibitory effect of DHQ on the ROS production resulting from the neutrophils activation by 100 ng/ml PMA. Numerical data are detailed in Table 2.

ROS production by neutrophils triggered by PMA 100 ng/mL (experimental data corresponding to FIG. 2).

| Integral | Peak max cpm | Slope max cpm | T. Slope max | T. half (rise) | T. max (peak) | T. half (fall) | Smoot Facto |
|---|---|---|---|---|---|---|---|
| 2.150E+09 | 1.196E+08 | 6.991E+07 | 0.67 | 0.22 | 3.33 | > | 0 |
| 3.576E+07 | 2.260E+06 | 1.033E+06 | 4.66 | 4.89 | 11.55 | > | 0 |
| 2.0172E+08 | 1.134E+07 | 4.380E+06 | 1.55 | 2.22 | 9.55 | > | 0 |
| 4.509E+08 | 2.430E+07 | 9.790E+06 | 1.78 | 2.44 | 11.77 | > | 0 |

Similarly, neutrophils were triggered by fMLP ($10^{-6}$ M) in the presence of different concentrations of DHQ (0, 1, 10 and 100 μM) at 37° C. in Hanks buffer containing 10 μM luminol and chemiluminescence was measured by a chemiluminometer. Total chemiluminescence counts during 22.21 min. (integrals) corresponding to total ROS production were determined. The corresponding results are presented in Table 3 and FIG. 3.

TABLE 3

Figure 3:
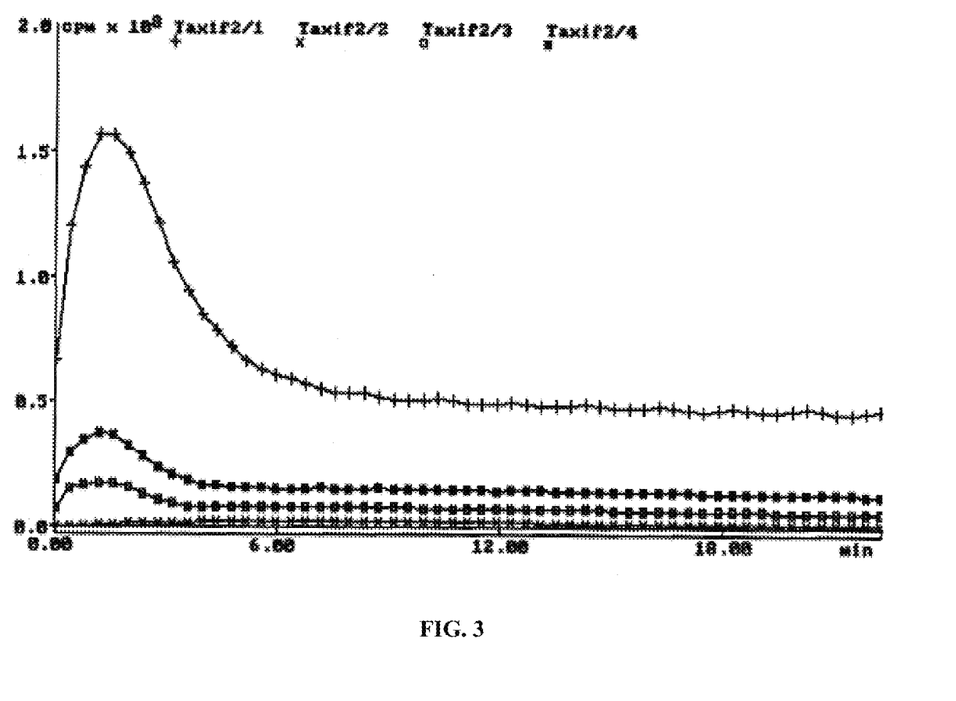
FIG. 3 is a graph showing the inhibitory effect of DHQ on the ROS production resulting from the neutrophils activation by $10^{-6}$ M fMLP. Numerical data are detailed in Table 3.

ROS production by neutrophils triggered by fMLP ($10^{-6}$M) (experimental data corresponding to FIG. 3).

| Integral | Peak max cpm | Slope max cpm | T. Slope max | T. half (rise) | T. max (peak) | T. half (fall) | Smoot Facto |
|---|---|---|---|---|---|---|---|
| 1.453E+09 | 1.571E+08 | 9.691E+07 | 0.22 | < | 1.55 | 4.44 | 0 |
| 4.329E+07 | 2.533E+06 | 1.464E+06 | 2.00 | 1.55 | 6.00 | > | 0 |
| 1.867E+08 | 1.770E+07 | 1.206E+07 | 0.22 | < | 1.33 | 3.55 | 0 |
| 3.838E+08 | 3.731E+07 | 2.492E+07 | 0.22 | < | 1.33 | 3.78 | 0 |

The chemiluminescent assay detected all oxidizing ROS including the protonated form of superoxide anion and hydrogen peroxide.

The results of FIGS. 2 and 3 show that DHQ strongly inhibits the ROS production by neutrophils activated either by PMA or fMLP. The inhibitory effect provided by DHQ appears very efficient since the addition of 1 μM in the assay medium results in around 80% inhibition of the ROS production in both experiments.

These results thus suggest that DHQ, in addition to its well-known antioxidant property, inhibits the NADPH oxidase activation in polymorphonuclear neutrophils triggered by either fMLP or PMA. This property is confirmed by the fact that DHQ further strongly inhibits the oxygen consumption of polymorphonuclear neutrophils triggered by PMA and fMLP (data not shown).

Example 3: Effect of DHQ on the Activation of Mast Cells

Materials and Methods

Pure populations of human mast cells (HMC) are obtained by long-term culture of human normal hematopoietic progenitors ($CD34^+$ cells) in the continuous presence of Stem Cell Factor (SCF). Sources of these $CD34^+$ cells are mainly bone marrow, cord blood or peripheral blood. Usually, mononuclear cells from bone marrow and cord blood contain 0.5-1% of $CD34^+$ cells, whereas peripheral blood contains less than 0.1% of $CD34^+$ cells.

Hematopoietic progenitor cells can be rapidly and efficiently enriched to a purity of about 85-98% using positive selection of magnetically labeled $CD34^+$ cells. Hematopoietic progenitor cells are then magnetically labeled using MACS CD34 MicroBeads. The magnetically labeled cells are enriched on positive selection columns in the magnetic field. Mononuclear cells from peripheral blood (PBMC), cord blood, or bone marrow may otherwise be obtained by density gradient centrifugation over Ficoll Paque®. Fractionation methods for producing mast cells are described in the art (see for instance Arock et al., 2008, Methods in Molecular biology 415: 241-254).

Results

Figure 4:
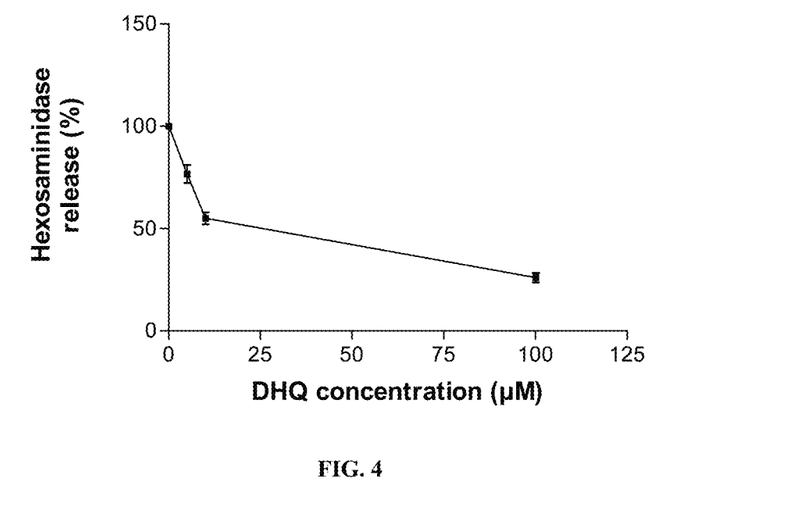
FIG. 4 is a graph showing the effect of DHQ on mast cell degranulation as estimated by beta-hexosaminidase release. Decrease of released beta-hexaminidase is expressed in percents, with 100% corresponding to the beta-hexaminidase release in absence of DHQ. Concentration of DHQ is reported in μM.

Mast cell degranulation was induced by sequential treatment of mast cell by IgE, then by anti-IgE antibodies. Degranulation was subsequently measured by evaluating the release of beta-hexosaminidase, 1 h after IgE stimulation (see FIG. 4).

The experiments performed demonstrate that DHQ has a strong inhibitory activity on degranulation of mast cells (80% inhibition at 100 μM and up to 50% at 10 μM). This result indicates that DHQ displays a high inhibitory activity, which is superior to kinase inhibitors and chromoglycate (reference molecule).

Example 3: Effect of DHQ on NIH-3T3 Fibroblasts Proliferation

Materials and Methods

The NIH 3T3 cell line was purchased from the ATCC (CRL1658). Cell lines are grown in Dulbecco's Modified Eagles' Medium (DMEM) supplemented with 10% heat inactivated newborn calf serum, 100 UI/mL penicillin and 100 μg/mL streptomycin (all from Gibco BRL) at 37° C. in a humidified 5% $CO_2$ atmosphere. DHQ is dissolved in DMSO. Cells are cultured during 48 hours in the absence or in the presence of various DHQ concentrations. NIH-3T3 fibroblasts are immortalized cells which mimic the inflammatory phenotype assessed by the abundance of actin stress fibers and high contractility.

The effects of DHQ on the growth of NIH-3T3 cells are determined using the 3-(4,5-dimetthylthiazol-2-yl)-2,5-diphenyltetrazolium bromide (MTT) assay. Briefly, cells are plated on 96 well plates at 4,000 cells per well with increasing DHQ concentrations. After 72 hours of incubation with the drug, medium is removed and replaced by complete medium+MTT (10% v/v). After 3 hours of incubation, formazan crystals are dissolved in buffer containing 10% SDS (w/v, Bio-Rad), 50% Dimethyl formamide (Sigma), pH 4.7. Absorbance of reduced formazan is measured at 580 nm. Results are presented in FIG. 5: 100% of MTT reduced is attributed to the measure performed in absence of DHQ.

Results

Figure 5:
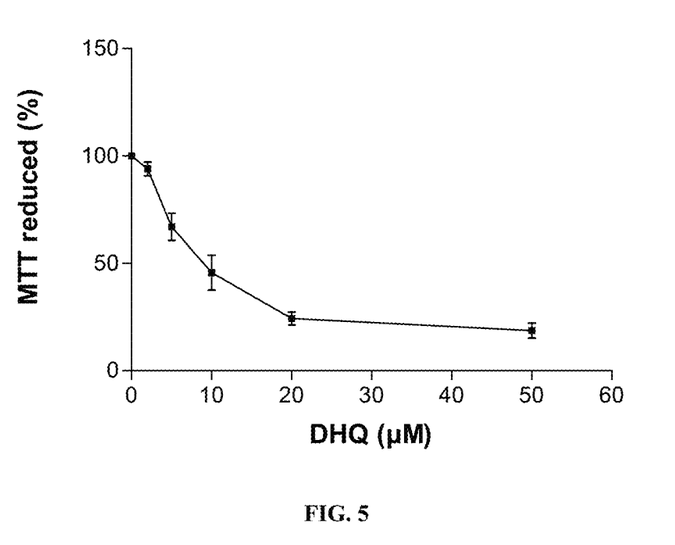
FIG. 5 is a graph showing the inhibition of fibroblasts proliferation in the presence of increasing concentrations of DHQ as estimated by the decrease of reduced MTT levels. Decrease of reduced MTT levels is evaluated by measure of reduced formazan. Cell viability is assessed by the extent of MTT reduced. Concentration of DHQ is reported in μM.

As shown in FIG. 5, cell viability of NIH-3T3 cells cultured in the presence of increasing DHQ concentrations is reduced (cell viability is assessed by the extent of MTT reduced). Considering that NIH-3T3 fibroblasts are immortalized cells which mimic the myofibroblasts phenotype, it can therefore be inferred from these results that fibroblast proliferation is inhibited in the presence of increasing concentrations of DHQ.

Example 4

Some parameters of symptoms were collected in a group of 20 male subjects suffering from genital herpes simplex virus type 2 recrudescences (three to five outbreaks a year), and showing HSV-2 induced mucosal inflammation and genital blisters and sores, with itching. A first group of five subjects (Group A) were treated, during 14 days by topically applying once a day a composition comprising:
5% w/w DHQ
1% w/w α-tocopherol
0.2% w/w bisabolol.

A second group of five subjects (Group B) were treated during 14 days by topically applying once a day a composition comprising 5% w/w α-dihydroquercetin as single active agent.

A third group of five subjects (Group C) were treated during 14 days by topically applying once a day a composition comprising 1% w/w α-tocopherol as single active agent.

A fourth group of five subjects (Group D) were treated during 14 days by topically applying once a day a composition 0.2% w/w bisabolol as single active agent.

Group A reported a strong and both immediate and long-time relief of the inflammation and pain, a diminution of the numbers of blisters and sores. It was also noted a longer time before the following outbreak comes up.

Group B reported an effect on the number of blisters and sores after 7 days, and a relief of associated inflammation.

Group C reported a sensation of relief upon application of the α-tocopherol composition, during about 10 minutes to one hour. Beyond this immediate relief, no alleviation of symptoms was reported.

Group D reported an absence of any effect.

CONCLUSION

The association in a single combination of DHQ, α-tocopherol and bisabolol seems to bring a synergic effect in terms of penetration and immediate relief of inflammation of the patients, combined with an immediate onset of the action of DHQ, followed up by a mid-term and long-term action of DHQ. This effect is not observable in groups having been administered with single ingredients.

The invention claimed is:

1. A method for treating genital sores or blisters in subjects suffering from genital herpes simplex virus type 2 infection, comprising topically administering once a day during 14 days an effective amount of a composition comprising 5% w/w dihydroquercetin, 1% w/w α-tocopherol, 0.2% w/w bisabolol and a mucosal-compatible base.

2. The method according to claim 1, wherein the mucosal compatible base in said composition comprises at least one compound selected from the group consisting of animal fat, vegetable fat, higher alcohols, glycols, and mixtures thereof.

3. The method according to claim 1, wherein said composition further comprises at least one component selected from the group consisting of surfactants, pigments, stabilizers, emollients, humectants, and mixtures thereof.

4. The method according to claim 1, wherein the composition is a cream, a gel, an ointment, a solution, an emulsion, an oil-in-water emulsion, a mask, a stick, a milk, a lotion, a serum, a paste, a foam, or a suspension.

5. The method according to claim 1, wherein the composition is a cream.

6. The method according to claim 1, wherein the composition is formulated as a stick.

7. The method according to claim 1, wherein the composition is administered in combination with another treatment for herpes.

8. The method according to claim 1, wherein the composition is administered in combination with an oral treatment for herpes.

* * * * *